(12) United States Patent
Miura et al.

(10) Patent No.: US 11,517,603 B2
(45) Date of Patent: Dec. 6, 2022

(54) BONE REMODELING ACCELERATOR

(71) Applicant: HOKURIKU UNIVERSITY, Kanazawa (JP)

(72) Inventors: Masakazu Miura, Kanazawa (JP); Tatsuo Takahashi, Kanazawa (JP); Hirokazu Suzuki, Kanazawa (JP); Yukio Kawata, Kanazawa (JP); Shoko Kitade, Kanazawa (JP); Mako Takenaka, Kanazawa (JP); Masanori Ohmoto, Kanazawa (JP); Yuki Sato, Kanazawa (JP)

(73) Assignee: HOKURIKU UNIVERSITY, Kanazawa (JP)

( * ) Notice: Subject to any disclaimer, the term of this patent is extended or adjusted under 35 U.S.C. 154(b) by 10 days.

(21) Appl. No.: 16/649,059

(22) PCT Filed: Sep. 20, 2018

(86) PCT No.: PCT/JP2018/034808
§ 371 (c)(1),
(2) Date: Mar. 19, 2020

(87) PCT Pub. No.: WO2019/059275
PCT Pub. Date: Mar. 28, 2019

(65) Prior Publication Data
US 2020/0268818 A1 Aug. 27, 2020

(30) Foreign Application Priority Data
Sep. 21, 2017 (JP) ............................. JP2017-181670

(51) Int. Cl.
*A61K 36/48* (2006.01)
*A61K 31/353* (2006.01)

(52) U.S. Cl.
CPC ............ *A61K 36/48* (2013.01); *A61K 31/353* (2013.01); *A61K 2236/333* (2013.01)

(58) Field of Classification Search
CPC .................................................... A61K 36/48
See application file for complete search history.

(56) References Cited

U.S. PATENT DOCUMENTS

| | | | |
|---|---|---|---|
| 4,617,293 A | 10/1986 | Wahlig et al. |
| 2005/0215493 A1 | 9/2005 | Miyake et al. |
| 2014/0213535 A1 | 7/2014 | Maurya et al. |

FOREIGN PATENT DOCUMENTS

| | | | | |
|---|---|---|---|---|
| EP | 3207935 A1 | * | 5/2017 | ........... A61K 8/9789 |
| FR | 3005419 A1 | * | 11/2014 | ............. A61K 45/06 |
| JP | 2001-072598 A | | 3/2001 | |
| JP | 2002-234844 A | | 8/2002 | |
| JP | 2003-026572 A | | 1/2003 | |
| JP | 4426674 B2 | * | 3/2010 | |
| JP | 2013-184961 A | | 9/2013 | |
| JP | 2014-001201 A | | 1/2014 | |
| JP | 2014-152129 A | | 8/2014 | |
| JP | 2015-181366 A | | 10/2015 | |
| JP | 2015-182960 A | | 10/2015 | |
| RU | 2320346 C2 | * | 3/2008 | .............. A61P 19/08 |

OTHER PUBLICATIONS

The Plant List (http://www.theplantlist.org/tpl1.1/record/ild-33335), Jul. 4, 2010 (Year: 2010).*
World Flora Online http://www.worldfloraonline.org/taxon/wfo-0000186843 (Year: 2017).*
JP-4426674-B2 translated (Year: 2010).*
RU-2320346-C2 translated (Year: 2008).*
FR-3005419-A1 translated (Year: 2014).*
Kang (3'4'7-Trihydroxyflavone inhibits RANKL-induced osteoclast formation via NFATc1, College of Pharmacy, Sookmyung Women's University, Seoul, Republic of Korea, Pharmazie 70: 661-667, Apr. 10, 2015) (Year: 2015).*
Habauzit et al., "Differential effects of two citrus flavanones on bone quality in senescent male rats in relation to their bioavailabity and metabolism," *Bone*, 49(5):1108-1116 (2011).
Wang et al., "Effects of Eleven Flavonoids from the Osteoprotective Fraction of *Drynaria fortunei* (Kunze) J. SM. on Osteoblastic Proliferation Using an Osteoblast-Like Cell Line," *Chem. Pharm. Bull.*, 56(1): 46-51 (2008).
Japanese Patent Office, International Search Report in International Patent Application No. PCT/JP2018/034808 (dated Dec. 11, 2018).
European Patent Office, Extended European Search Report in European Patent Application No. 18859747.0 (dated May 3, 2021).
Kang et al., "3',4',7,8-Tetrahydroxyflavone Inhibits RANKL—induced Osteoclast Formation and Bone Resorption," *Pharmazie*, 72(3): 161-166 (2017).
Japan Patent Office, Notice of Reasons for Refusal in Japanese Patent Application No. 2019-543698 (dated Jun. 7, 2022).

* cited by examiner

*Primary Examiner* — Terry A McKelvey
*Assistant Examiner* — Jacob A Boeckelman
(74) *Attorney, Agent, or Firm* — Leydig, Voit & Mayer, Ltd.

(57) ABSTRACT

The present invention provides a preventing or improving agent that can favorably promote bone formation, is effective in preventing or improving osteoporosis or a decrease in bone strength, has high safety, and is suitable for long-term continuous ingestion or administration, by forming a bone remodeling accelerator comprising one or more kinds selected from the group consisting of flavanone and a glycoside thereof.

6 Claims, 4 Drawing Sheets

BONE REMODELING ACCELERATOR

CROSS-REFERENCE TO RELATED APPLICATIONS

This patent application is the U.S. national phase of International Patent Application No. PCT/JP2018/034808, filed Sep. 20, 2018, which claims the benefit of Japanese Patent Application No. 2017-181670, filed on Sep. 21, 2017, which are incorporated by reference in their entireties herein.

TECHNICAL FIELD

The present invention relates to a bone remodeling accelerator useful for preventing or improving osteoporosis or a decrease in bone strength.

BACKGROUND ART

Osteoporosis is defined as a bone-metabolic disease with an increased risk of bone fracture which is characterized by a decrease in bone strength.

Bone strength varies depending on the bone mass and bone quality. Bone undergoes remodeling in which bone resorption by osteoclasts and bone formation by osteoblasts are repeated even after the growth period, and 20% to 30% of bones are replaced with new bone in one year. When this remodeling is out of balance and bone resorption exceeds bone formation, bone mass decreases.

In addition, bone quality decreases due to changes in the microstructure of the bone (micro damage), accumulation of microfractures, deterioration of bone-forming components such as collagen, and the like It is known that such decrease in the bone mass and bone quality may be caused by aging; hormonal imbalance due to a decrease in the secretion of female hormones (estrogen) and the like; nutritional imbalance due to lack of calcium, protein, vitamin D, vitamin K, etc., decrease in nutrient absorption, and the like; lack of exercise; smoking; drinking; diseases such as endocrine system disease, diabetes, rheumatoid arthritis and the like; drugs such as steroid drug and the like; and the like.

In osteoporosis patients, the risk of bone fracture increases even by a slight impact such as a fall down and the like. Particularly, in the case of the elderly people, bone fracture often leads to the need for nursing care. Therefore, it is important to treat, improve, and prevent osteoporosis.

As treatment methods for osteoporosis, a dietary treatment including actively ingesting calcium and protein, which are the main components of bone, vitamin D and vitamin K necessary for bone remodeling, and the like and trying to take a balanced meal, exercise therapy including performing moderate intensity exercises or continuously performing back muscle training such as walking, aerobics, and the like; and drug therapy using bisphosphonate preparations such as sodium alendronate hydrate, risedronate sodium hydrate, ibandronate sodium hydrate, zoledronic acid hydrate and the like, selective estrogen receptor modulator (SERM) preparations such as raloxifene hydrochloride and the like, a drug that prevents bone absorption and increases bone mass such as anti-RANKL (Receptor activator of nuclear factor kappa-B ligand) monoclonal antibody preparations) (e.g., denosumab) and the like, a drug that accelerates bone formation and increases bone mass such as parathyroid hormone preparation (e.g., teriparatide and the like), a drug that promotes bone metabolism such as active vitamin $D_3$ preparation (e.g., alfacalcidol, calcitriol, eldecalcitol), vitamin $K_2$ (e.g., menatetrenone), and the like are being performed.

In addition, as a component that increases bone density, promotes bone formation, has an effect of preventing or improving abnormal bone metabolism, and can also be ingested as food, many suggestions have been made such as whey protein hydrolysate (patent document 1), ascorbic acid phosphate magnesium salt, ascorbic acid derivative such as ascorbic acid-2-glucoside and the like (patent document 2), menaquinone-7 (patent document 3), Eisenia bicyclis extract (patent document 4), shark nose cartilage proteoglycan (patent document 5) and the like.

Furthermore, it has been reported that an extract of *Chamaecrista nomame*, which has long been used as a folklore medicine, with a solvent selected from ethanol, water and a mixture thereof has an effect of inhibiting bone resorption (patent document 6).

However, for example, bisphosphonate preparations used as therapeutic drugs for osteoporosis are known to suppress not only bone resorption but also bone formation, and hormone preparations such as parathyroid hormone preparation and the like are feared to express a hormone-like action besides bone formation promoting and bone mass increasing action.

As a prophylactic or therapeutic drug for osteoporosis, one not only showing suppression of bone resorption as the main effect but also capable of actively promoting bone formation, having high safety, and permitting continuous ingestion or administration for a long period of time is demanded. However, only a few of the components reported to have a bone formation promoting action have been confirmed to have sufficient safety and efficacy.

Accordingly, there is a demand for a highly safe agent for preventing or improving osteoporosis that can not only suppress bone resorption but also promote bone formation.

DOCUMENT LIST

Patent Documents patent document 1: JP-A-2013-184961
patent document 2: JP-A-2014-001201
patent document 3: JP-A-2015-181366
patent document 4: JP-A-2014-152129
patent document 5: JP-A-2015-182960
patent document 6: JP-A-2001-072598

SUMMARY OF INVENTION

Technical Problem

Thus, the present invention aims to provide a preventing or improving agent that can favorably promote bone formation, is effective in preventing or improving osteoporosis or a decrease in bone strength, has high safety, and is suitable for long-term continuous ingestion or administration.

Solution to Problem

The present inventors have conducted intensive studies in an attempt to solve the aforementioned problems and found that flavanone and a glycoside thereof have an action of favorably accelerating bone remodeling, are highly safe, and are useful for preventing or improving osteoporosis or decrease in bone strength, which resulted in the completion of the present invention.

That is, the present invention relates to the following.
[1] a bone remodeling accelerator comprising one or more kinds selected from the group consisting of flavanone and a glycoside thereof.
[2] The bone remodeling accelerator of [1], wherein the flavanone and the glycoside thereof are flavanone of a plant belonging to the genus *Chamaecrista* and a glycoside thereof.
[3] The bone remodeling accelerator of [1], wherein the one or more kinds selected from the group consisting of flavanone and a glycoside thereof is contained as an extract of a plant belonging to the genus *Chamaecrista* in methanol and ethyl acetate.
[4] The bone remodeling accelerator of any of [1] to [3], wherein the flavanone and a glycoside thereof are 3',4',7-trihydroxyflavanone and a glycoside thereof.
[5] A pharmaceutical product for preventing or improving osteoporosis or a decrease in bone strength, comprising the bone remodeling accelerator of any of [1] to [4].
[6] A food composition for preventing or improving osteoporosis or a decrease in bone strength, comprising the bone remodeling accelerator of any of [1] to [4].
[7] A commercial package comprising the bone remodeling accelerator of any of [1] to [4] and a written matter associated therewith, the written matter stating that the accelerator can or should be used for accelerating bone remodeling, or preventing or improving osteoporosis or a decrease in bone strength.
[8] A method for accelerating bone remodeling, comprising ingestion by or administration to a target animal in need of acceleration of bone remodeling of one or more kinds selected from the group consisting of flavanone and a glycoside thereof in an amount effective in accelerating bone remodeling.
[9] The method of [8], wherein the flavanone and the glycoside thereof are flavanone of a plant belonging to the genus *Chamaecrista* and a glycoside thereof.
[10] The method of [8], wherein the one or more kinds selected from the group consisting of flavanone and a glycoside thereof is contained as an extract of a plant belonging to the genus *Chamaecrista* in methanol and ethyl acetate.
[11] The method of any of [8] to [10], wherein the flavanone and a glycoside thereof are 3',4',7-trihydroxyflavanone and a glycoside thereof.
[12] A method for preventing or improving osteoporosis or a decrease in bone strength, comprising ingestion by or administration to a target animal in need of prevention or improvement of osteoporosis or a decrease in bone strength of one or more kinds selected from the group consisting of flavanone and a glycoside thereof in an amount effective in preventing or improving osteoporosis or a decrease in bone strength.
[13] The method of [12], wherein the flavanone and the glycoside thereof are flavanone of a plant belonging to the genus *Chamaecrista* and a glycoside thereof.
[14] The method of [12], wherein the one or more kinds selected from the group consisting of flavanone and a glycoside thereof is contained as an extract of a plant belonging to the genus *Chamaecrista* in methanol and ethyl acetate.
[15] The method of any of [12] to [14], wherein the flavanone and a glycoside thereof are 3',4',7-trihydroxyflavanone and a glycoside thereof.

Advantageous Effects of Invention

According to the present invention, a bone remodeling accelerator that can favorably accelerate differentiation of both osteoblast and osteoclast, and can accelerate bone remodeling by promoting bone resorption and bone formation in good balance can be provided.

The bone remodeling accelerator of the present invention accelerates bone metabolism and is useful for preventing or improving osteoporosis or a decrease in bone strength.

DESCRIPTION OF EMBODIMENTS

The present invention provides a bone remodeling accelerator (hereinafter to be also referred to as "the agent of the present invention" in the present specification).

The agent of the present invention contains one or more kinds selected from the group consisting of flavanone and a glycoside thereof.

In the present invention, the "bone remodeling accelerator" is a component or composition that has a bone remodeling accelerating action and can be contained in a pharmaceutical product for preventing or improving osteoporosis and the like.

Flavanone contained in the agent of the present invention is a compound having a flavanone skeleton shown by the following formula (1), and a glycoside thereof is typically a 15 compound glycosylated at the 7-position.

(1)

In the present invention, as flavanone and a glycoside thereof, a desired compound may be synthesized by a known enantio selective chemical synthesis method, a biochemical synthesis method or the like, or may be extracted from a plant etc. containing them, isolated, purified and used. The flavanone and a glycoside thereof may also be used in the form of an extract obtained from a plant and the like or a crude purified product.

As a plant containing flavanone or a glycoside thereof, a plant belonging to the genus *Chamaecrista* is recited as an example of a preferable plant, and *Chamaecrista nomame* (Siebold) H. Ohashi is more preferable.

*Chamaecrista nomame* (Siebold) H. Ohashi is an annual plant belonging to the family Leguminosae, subfamily Caesalpinioideae, genus *Chamaecrista*, and has long been used as Kobo tea, hama tea and as a folk medicine for diuresis.

Flavanone and a glycoside thereof obtained by extracting with an extraction solvent from the plant body of a plant belonging to the genus *Chamaecrista* such as *Chamaecrista nomame* and the like are preferably used for the agent of the present invention.

The plant body of the plant belonging to the genus *Chamaecrista* is washed with water and directly subjected to extraction, or extracted in the form of a slurry, fine granules, granules, or powder by performing chopping, drying, pulverizing and the like.

For extraction, respective parts such as flower, leave, stem, fruit, root and the like of a plant belonging to the genus *Chamaecrista* can be used, and it is preferable to use above-ground parts excluding fruits.

As the extraction solvent, water and polar organic solvents such as lower alcohol (e.g., methanol, ethanol, propanol, isopropanol, butanol etc.), polyhydric alcohol (e.g., propanediol, butanediol, glycerol etc.), ester of low-molecular-weight carboxylic acid (ethyl acetate etc.), ketone (acetone etc.) and the like can be used. One kind of these may be used alone, or two or more kinds thereof may be used in combination.

For the purpose of the present invention, lower alcohol such as methanol, ethanol and the like, and ester of low-molecular-weight carboxylic acid such as ethyl acetate and the like are preferably used, and methanol and ethyl acetate are more preferably used.

The extraction solvent is used in an amount of typically 100 mL-1000 mL, preferably 400 mL-1000 mL, per 100 g (dry weight) of the plant body of a plant belonging to the genus *Chamaecrista*.

Extraction can be performed by immersing the plant body of a plant belonging to the genus *Chamaecrista* in the above-mentioned extraction solvent, and standing same as it is or stirring same. Also, it may be performed by disrupting the plant body of a plant belonging to the genus *Chamaecrista* in an extraction solvent or homogenizing the plant body in an extraction solvent by the use of a bead-type crushing device or the like.

The extraction temperature and extraction time can be appropriately determined according to the method of pretreatment of the plant body of a plant belonging to the genus *Chamaecrista*, the kind of extraction solvent, extraction method and the like. For example, when extraction includes immersing in an extraction solvent containing lower alcohol, the extraction is typically performed at 70° C.-80° C. for 1 hr-4 hr, or preferably at 70° C.-80° C. for 2 hr-4 hr.

After extraction, the extract is recovered by a conventional method, for example, filtration, centrifugation and the like.

In the agent of the present invention, flavanone and a glycoside thereof extracted from a plant belonging to the genus *Chamaecrista* can also be used in the form of being contained in the extract of the plant belonging to the genus *Chamaecrista*. They can also be used as a fraction containing these as the main component which is obtained by crude purification or purification according to a conventional method, or as an isolated form of flavanone or a glycoside thereof.

The crude purification or purification of flavanone or a glycoside thereof from an extract of a plant belonging to the genus *Chamaecrista* can be performed by combining concentration, separation by column chromatography such as silica gel chromatography, size-exclusion chromatography and the like, reversed-phase silica gel chromatography, high performance liquid chromatography (HPLC) and the like, and the like of the extract.

A preferable flavanone is, for example, 3',4',7-trihydroxyflavanone (butyne), a preferable flavanone glycoside is, for example, glycoside of the aforementioned flavanone, and a particularly preferable flavanone glycoside is, for example, 3',4',7-trihydroxyflavanone 7-O-β-D-glucopyranoside.

The agent of the present invention may contain one or more kinds selected from the group consisting of various flavanones and glycosides thereof such as flavanone and a glycoside thereof synthesized by a chemical synthesis method or a biochemical synthesis method, and flavanone and a glycoside thereof obtained by extracting from various plants such as a plant belonging to the genus *Chamaecrista* and the like.

The agent of the present invention can be prepared by adding as necessary general additives used in the field of preparation making to one or more kinds selected from the group consisting of flavanone and a glycoside thereof (hereinafter sometimes referred to as "flavanones" in the present specification), and according to a formulating means well known in the field of preparation making, for example, the method described in the Japanese Pharmacopoeia 17th edition, General Rules for Preparations [3] each preparation section and the like, and can be prepared as a liquid form such as solution, suspension, emulsion and the like; a semi-solid form such as gel, paste, cream and the like; a solid form such as powder, granule, tablet, capsule and the like, or the like.

Examples of the above-mentioned additive include excipient, binder, disintegrant, lubricant, coating agent, base, solvent, emulsifier, dispersing agent, suspending agent, stabilizer, thickening agent, pH adjuster, antioxidant, antiseptic, preservative, corrigent, sweetening agent, flavor, colorant and the like.

Examples of the excipient include silicic anhydride, m calcium silicate, magnesium silicate aluminate, starch (cornstarch, potato starch, wheat starch etc.), saccharides (glucose, lactose, sucrose etc.), sugar alcohol (sorbitol, maltitol, mannitol etc.) and the like.

Examples of the binder include gelatin, casein sodium, starch and processed starch (cornstarch, hydroxypropyl starch, pregelatinized starch, partly pregelatinized starch etc.), cellulose and a derivative thereof (crystalline cellulose, hydroxypropylcellulose, carboxymethylcellulose etc.) and the like.

Examples of the disintegrant include povidone, crospovidone, cellulose and a derivative thereof (crystalline cellulose, methylcellulose etc.) and the like.

Examples of the lubricant include talc, synthesis aluminum silicate, magnesium silicate, calcium stearate, magnesium stearate and the like.

Examples of the coating agent include methacrylic acid copolymer (methacrylic acid·ethyl acrylate copolymer etc.), methacrylate copolymer (ethyl acrylate-methyl methacrylate copolymer, ethyl acrylate-methyl methacrylate-methacrylic acid trimethylammonium chloride ethyl copolymer etc.) and the like.

Examples of the base include hydrocarbon (liquid paraffin etc.), polyethylene glycol (macrogol 400, macrogol 1500 etc.) and the like.

Examples of the solvent include purified water, monovalent alcohol (ethanol etc.), polyhydric alcohol (propylene glycol, glycerol etc.) and the like.

Examples of the emulsifier include non-ionic surfactant (sorbitan fatty acid ester, glycerol fatty acid ester, polyoxyethylene sorbitan fatty acid ester, sucrose fatty acid ester etc.), anionic surfactant (alkylsodium sulfate, N-acylglutamate etc.), purified soybean lecithin and the like.

Examples of the dispersing agent include gum arabic, alginic acid propyleneglycol, non-ionic surfactant (polyoxyethylene hydrogenated castor oil, polyoxyethylene sorbitan fatty acid ester, polyoxyethylene polyoxypropylene glycol etc.), anionic surfactant (sodium alkylsulfate etc.) and the like.

Examples of the suspending agent include sodium alginate, non-ionic surfactant (polyoxyethylenelauryl ether, glycerol fatty acid ester, polyoxyethylene sorbitan fatty acid ester, propylene glycol ester of fatty acid etc.) and the like.

Examples of the stabilizer include adipic acid, ethylenediamine tetraacetate (calcium disodium ethylenediamine tetraacetate, disodium ethylenediamine tetraacetate etc.), α-cyclodextrin, β-cyclodextrin and the like.

Examples of the thickening agent include water-soluble polymer (sodium polyacrylate, carboxyvinyl polymer etc.), polysaccharides (sodium alginate, xanthan gum, tragacanth etc.) and the like.

Examples of the pH adjuster include hydrochloric acid, phosphoric acid, acetic acid, citric acid, lactic acid, sodium hydroxide, sodium hydrogenphosphate and the like.

Examples of the antioxidant include dibutylhydroxytoluene (BHT), butylhydroxyanisole (BHA), dl-α-tocopherol, erythorbic acid, propyl gallate and the like.

Examples of the antiseptic include sodium benzoate, sorbic acid, potassium sorbate, dehydroacetic acid, sodium dehydroacetate, paraoxybenzoate (methyl paraoxybenzoate etc.) and the like.

Examples of the preservative include benzoic acid, sodium benzoate, sorbitol, paraoxybenzoate (methyl paraoxybenzoate etc.), propylene glycol and the like.

Examples of the corrigent include ascorbic acid, erythritol, disodium 5'-guanylate, citric acid, sodium L-glutamate, tartaric acid, DL-malic acid and the like.

Examples of the sweetening agent include aspartame, licorice extract, saccharin and the like.

Examples of the flavor include orange essence, l-menthol, d-borneol, vanillin, linalool and the like.

Examples of the colorant include tar pigment (Food Color Red No. 2, Food Color Blue No. 1, Food Color yellow No. 4 etc.), inorganic pigment (red iron oxide, yellow ferric oxide, titanium oxide etc.), natural dye (annatto dye, turmeric dye, carotenoid etc.) and the like.

One or more kinds of the above-mentioned additives can be used as necessary.

The agent of the present invention can accelerate bone remodeling and promote bone metabolism by favorably accelerating differentiation of both osteoblast and osteoclast, and promoting bone resorption and bone formation in good balance.

As a result, the agent of the present invention is effective in preventing or improving osteoporosis or a decrease in bone strength, and is preferably applied to osteoporosis patients or those showing a decrease in bone strength and having a risk of developing osteoporosis due to exacerbation of hormone balance and nutritional state, and the like.

Furthermore, flavanones contained in the agent of the present invention are mainly components obtained from plants such as *Chamaecrista nomame* and the like, which have long been consumed as health tea, and have high safety.

Therefore, the agent of the present invention can be continuously ingested or administered for a long period of time.

The content of flavanone in the agent of the present invention is appropriately determined according to the kind thereof, strength of the bone remodeling acceleration action thereof and the like. It is preferably 0.01 wt %-100 wt %, more preferably 0.05 wt %-100 wt %, based on the total amount of the agent of the present invention.

The daily ingestion amount or dose of the agent of the present invention is appropriately determined according to the sex, age of the target who receives application (hereinafter to be also referred to as "application target" in the present specification), the state and level of a decrease in bone strength observed in the application target, and the form, administration method and the like of the agent of the present invention. When the application target is a human adult, the amount of flavanone is preferably 3 mg-150 mg, more preferably 10 mg-100 mg, further preferably 10 mg-50 mg, still more preferably 15 mg-50 mg.

The above-mentioned amount may be ingested or administered once, or may be ingested or administered several times (e.g., 2-3 times) by portions per day.

In addition, the ingestion or dosing period of the agent of the present invention is also appropriately determined according to the state and level of a decrease in bone strength and the like of the application target. Considering that osteoporosis is a bone-metabolic disease caused by aging, hormone imbalance and the like, it is preferable to continue ingestion or administration of the agent of the present invention for a long period of time to prevent or improve osteoporosis.

The agent of the present invention can be prepared can be formulated as a unit package form. In the present specification, the "unit package form" means a form of one or more units with a particular amount (e.g., ingestion amount or dose per one time etc.) as one unit is/are filled in one container or packed in a package. For example, a unit package form with ingestion amount or dose per one time as one unit is referred to as "unit package form for ingestion amount or dose per one time". A container or package used for the unit package form can be appropriately selected according to the form and the like of the agent of the present invention. For example, paper container or bag, plastic container or bag, pouch, aluminum can, steel can, glass bottle, pet bottle, PTP (press through pack) package sheet and the like can be mentioned.

The application subject of the agent of the present invention includes, for example, mammals (e.g., human, monkey, mouse, rat, guinea pig, hamster, rabbit, cat, dog, bovine, horse, donkey, swine, sheep, etc.), birds (e.g., duck, chicken, goose, turkey, etc.) and the like.

When the agent of the present invention is applied to an application target animal (hereinafter to be also simply referred to as "target animal") other than human, the ingestion amount or dose of the agent of the present invention can be appropriately set according to the kind, sex, body weight and the like of the target animal.

The agent of the present invention can be provided as a pharmaceutical product (hereinafter to be also referred to as "the pharmaceutical product of the present invention" in the present specification) directly or by further adding the above-mentioned pharmaceutically acceptable additives.

The pharmaceutical product of the present invention can have a dosage form of oral preparation such as tablet, coating tablet, chewable tablet, pill, capsule, microcapsule, granule, fine granule, powder, elixir, lemonade, syrup, suspension, emulsion, oral jelly and the like, injection such as solution, suspension, emulsion and the like, solid injection to be used by dissolving or suspending when in use, injectable preparation such as transfusion, sustainable injection and the like, and the like.

As mentioned above, flavanones contained in the agent of the present invention are mainly obtained from plants suitable for drinking or eating such as *Chamaecrista nomame* and the like, which have long been consumed as health tea, and are suitable for oral ingestion. Therefore, the pharmaceutical product of the present invention can be preferably provided as an oral preparation.

The pharmaceutical product of the present invention may further contain a therapeutic drug for osteoporosis such as an active vitamin $D_3$ preparation (e.g., alfacalcidol, calcitriol and the like), vitamin $K_2$ preparation (e.g., menatetrenone and the like), and the like as long as the characteristics of the present invention are not impaired.

The pharmaceutical product of the present invention can be preferably administered to osteoporosis patients or those showing a decrease in bone strength and having a high risk of developing osteoporosis due to exacerbation of hormone balance and nutritional state, and the like.

The pharmaceutical product of the present invention is administered to the above-mentioned application target such that the amount of flavanones is the above-mentioned ingestion amount or dose per day.

Furthermore, the agent of the present invention can be ingested by adding to various foods. The food to which the agent of the present invention is added is not particularly limited, and may be any as long as it is a food in the form generally served for meals or dessert.

For example, the agent of the present invention is added to drinks such as tea, beverage water and the like, and a suitable flavor is added when desired, whereby a functional drink can be provided.

More specifically, the agent of the present invention can be added, for example, to beverage water such as tea drinks, fruit drinks and the like; tea such as green tea, black tea, Chinese tea and the like; dairy products such as milk, yogurt and the like; confectionery such as jelly, biscuit, candy, caramel, and the like, and the like.

The agent of the present invention is preferably added to the above-mentioned various foods in amounts to be ingested per day such that the amount of flavanones is the above-mentioned dose per day.

The agent of the present invention can be provided as a food composition (hereinafter to be also referred to as "the food composition of the present invention" in the present specification) directly or by adding general food additives as necessary and according to a general food production technique.

The food composition of the present invention can be prepared as various forms such as liquid, suspension, emulsified liquid, gel, cream, powder, granule, sheet, capsule, tablet and the like.

Furthermore, by adding the agent of the present invention to various food starting materials and adding general food additives as necessary, the food composition of the present invention can be prepared as various food forms such as beverage water (fruit juice drinks, sport drinks, coffee drinks, tea drinks etc.), tea (green tea, white tea, yellow tea, blue tea, tea, black tea, flower tea etc.), dairy product (lactic fermenting beverage, fermented milk, butter, cheese, yogurt, processed milk, defatted milk etc.), processed meat product (ham, sausage, hamburg etc.), fish pastry product (fish cake, tube-shaped fish sausage etc.), egg processed product (rolled omelet, egg tofu, Chawan-mushi etc.), soybean processed product (soybean paste, tofu, fermented soybean etc.), wheat processed product (bread, Japanese wheat noodles, pasta etc.), dried seafood (bonito, dried broth, dried young sardines, etc.), confectionery (cookie, biscuit, jelly, chewing gum, candy, caramel, ice cream, etc.), soup (miso soup, consommé soup, corn soup, potage, etc.), seasoning (dressing, Worcestershire sauce, mayonnaise etc.) and the like, and it is also possible to adapt a package form such as a bottled food, canned food or retort pouch food.

As the above-mentioned food additive, manufacturing agent (brine, binding agent etc.), thickening stabilizer (xanthan gum, sodium carboxymethylcellulose etc.), gelling agent (gelatin, agar, carrageenan etc.), gum base (vinyl acetate resin, jelutong, chicle etc.), emulsifier (glycerol fatty acid ester, sucrose fatty acid ester, saponin, lecithin etc.), preservative (benzoic acid, sodium benzoate, sorbic acid, potassium sorbate, ε-polylysine etc.), antioxidant (ascorbic acid, erythorbic acid, catechin etc.), glazing agent (shellac, paraffin wax, beeswax etc.), fungicide (thiabendazole, fludioxonil etc.), leavening agent (sodium hydrogen carbonate, glucono δ-lactone, alum etc.), sweetener (aspartame, acesulfame potassium, licorice extract etc.), bittering agent (caffeine, naringin, worm wood extract etc.), acidulant (citric acid, tartaric acid, lactic acid etc.), seasoning (sodium L-glutamate, disodium 5'-inosinate etc.), colorant (annatto dye, turmeric dye, gardenia dye etc.), flavor (synthetic flavor such as ethyl acetoacetate, anisealdehyde and the like, natural flavor such as orange, lavender and the like) and the like can be mentioned.

In the present invention, one or more kinds of the above-mentioned food additives can be used.

Furthermore, the food composition of the present invention may contain nutrients necessary for maintaining or increasing the bone strength, such as calcium, protein, vitamin D, vitamin $K_2$ and the like, and a food material containing such nutrients, as long as the characteristics of the present invention are not impaired.

The food composition of the present invention can be preferably ingested by osteoporosis patients, and those at a high risk of developing osteoporosis or having decreased bone strength such as those who tend to have hormonal imbalance (e.g., menopausal women), those who are in a malnourished state due to excessive dieting, and the like. In addition, it can be widely ingested by middle-aged people, pregnant women and the like for the purpose of preventing osteoporosis and a decrease in bone strength.

Therefore, the food composition of the present invention can also be provided as food with health claims such as food for specified health uses, food with nutrient function claims, indicated functional food and the like, special purpose foods such as food for sick people, food for pregnant women and the like, health supplement, dietary supplement and the like for preventing or improving osteoporosis or a decrease in bone strength.

The food composition of the present invention is preferably ingested by the above-mentioned application target such that the amount of flavanones is the above-mentioned ingestion amount per day.

The present invention can also provide a commercial package containing the above-mentioned agent of the present invention and a written matter associated therewith, the written matter stating that the agent can or should be used for accelerating bone remodeling, or preventing or improving osteoporosis or a decrease in bone strength.

The present invention further provides a method for accelerating bone remodeling in a target animal in need of acceleration of bone remodeling (hereinafter to be also referred to as "the acceleration method of the present invention" in the present specification).

The acceleration method of the present invention includes ingestion by or administration to a target animal in need of acceleration of bone remodeling flavanones in an amount effective in accelerating bone remodeling.

Furthermore, the present invention also provides a method for preventing or improving osteoporosis or a decrease in bone strength in a target animal in need of prevention or improvement of osteoporosis or a decrease in bone strength (hereinafter to be also referred to as the "preventing or improving method of the present invention" in the present specification).

The preventing or improving method of the present invention includes ingestion by or administration to, a target animal in need of prevention or improvement of osteoporosis or a decrease in bone strength, of flavanones in amounts effective for preventing or improving osteoporosis or a decrease in bone strength in the target animal.

The target animal in the above-mentioned acceleration method of the present invention and the preventing or improving method of the present invention includes mammal (e.g., human, monkey, mouse, rat, guinea pig, hamster, rabbit, cat, dog, bovine, horse, donkey, swine, sheep etc.), birds (e.g., duck, chicken, goose, turkey etc.) and the like.

The acceleration method of the present invention and the preventing or improving method of the present invention are effective in preventing or improving osteoporosis or a decrease in bone strength.

In the case of human, the acceleration method of the present invention and the preventing or improving method of the present invention are preferably applied to osteoporosis patients, or those having decreased bone strength due to deterioration of hormone balance and nutritional state, and the like, and at a high risk of developing osteoporosis.

The effective amount of flavanones in the acceleration method of the present invention and the preventing or improving method of the present invention is determined according to the kind, age, sex, the state and level of a decrease in bone strength and the like of the target animal. An amount similar to the above-mentioned ingestion amount or dose of the agent of the present invention for a human or a target animal other than human can be ingested or administered at the frequency and period mentioned above.

The ingestion or administration method of flavanones in the acceleration method of the present invention and the preventing or improving method of the present invention includes oral administration, injection, administration by infusion and the like. Oral administration is preferable since convenient ingestion is possible without the need to perform under the guidance and supervision of a doctor at a medical institution.

EXAMPLE

The present invention is explained in more detail by in the following by Experimental Example and the like.

Production Example 1

Preparation of Flavanone Glycoside from *Chamaecrista nomame*

The above-ground parts of *Chamaecrista nomame* (Siebold) H. Ohashi were washed with water and, after removing fruit, cut into a suitable length and dried at 50° C. The dried product of *Chamaecrista nomame* (1.33 kg) was heated in methanol (7 L) at 80° C. for 1 hr, and then heated in methanol (6 L) at 80° C. for 1 hr. The obtained methanol extract (253 g) was extracted 3 times with water-ethyl acetate, and the ethyl acetate layer was recovered to give an ethyl acetate extract (89.5 g).

The ethyl acetate extract (89.5 g) was separated by eluting with a methanol-water mixed solution and using Cosmosil 140C18-OPN column (manufactured by Nacalai Tesque) by gradually changing the methanol concentration at 40(v/v) %, 50(v/v) %, 60(v/v) %, 70(v/v) %, 80(v/v) %, 90(v/v) %, 100(v/v) %. The 4th to 22nd fractions (28.2 g in total) were recovered, and then separated by eluting with a methanol-water mixed solution and using TOYOPEARL HW-40 column (manufactured by Tosoh Corporation) by gradually changing the methanol concentration at 25(v/v) %, 30(v/v) %, 35(v/v) %, 40(v/v) %. The 30th to 40th fractions (610 mg) were recovered, separated by eluting with chloroform-methanol-water and using Wakogel C-200 column (manufactured by Wako Pure Chemical Industries, Ltd.) and the 82nd-88th fractions (160 mg) and the 89th-92nd fractions (160 mg) were recovered.

The recovered above-mentioned fractions were separated by HPLC under the following conditions to obtain peaks with retention time of 15 min and 27 min.

<HPLC Analysis Conditions>
column: Cosmosil 5C18AR-II (manufactured by Nacalai Tesque) (20 mm×250 mm)
mobile phase: methanol-water mixed solution (40:60 (volume ratio))
flow rate: 6 mL/min
detection: UV (210nm)

Two compounds with one peak which were obtained by HPLC analysis were recovered, and the structure was determined by nuclear magnetic resonance spectrum (NMR). For NMR measurement, the compound was dissolved in deuterated dimethyl sulfoxide (d6-DMSO), and 500 MHz nuclear magnetic resonance spectrometer "JNM-ECP500" (manufactured by JEOL Ltd.) was used.

As a result, a compound with a peak at retention time=15 min was a novel compound (F1). In addition, a compound with a peak at retention time=27 min was identified as flavanone glycoside, 3',4',7-trihydroxyflavanone 7-O-β-D-glucopyranoside, shown by the formula (2).

(2)

Experimental Example 1

Study of Influence of Flavanones Derived from *Chamaecrista nomame* on Differentiation of Osteoblast Influence of the flavanone glycoside (F2) derived from *Chamaecrista nomame* and obtained in the above-mentioned Production Example and aglycon thereof (3',4',7-trihydroxyflavanone shown by the following formula (3)) (F2a) on the differentiation of osteoblast was studied.

(3)

Mouse bone marrow cells were seeded in each well of a microplate containing 0.5 mL Eagle minimum essential medium a modified type (α-MEM) (manufactured by MP Biomedicals INC.) at $2.5 \times 10^6$ cells/well, and cultured at 37° C., carbon dioxide concentration=5(v/v)%. On day 1 of culture, each of F2 and F2a was added to a concentration of 1 µM, 2.5 µM, 5 µM or 10 µM, and culture was continued. On days 1 and 4 of culture, a differentiation induction reagent (0.2 mM ascorbic acid, 2.5 mM β-glycerophosphoric acid, 10 nM dexamethasone) was added to the following final concentrations. At 6 days from the culture, the cells were stained with alkaline phosphatase (ALP), observed with a microscope (inverted culture microscope "CK40", manufactured by Olympus Corporation, magnification=40×), and the osteoblast nodule stained with ALP, i.e., cell nodule formed by differentiated osteoblast, was detected. The case where neither F2 nor F2a was added was taken as a control.

Figure 1:
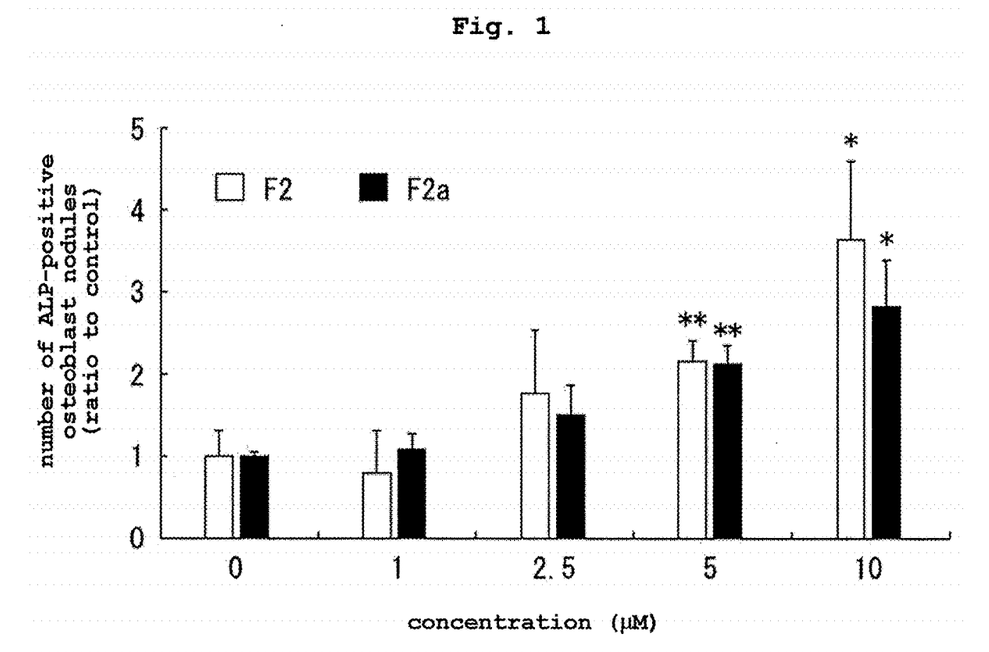
FIG. 1 shows the study results of Experimental Example 1. In the Figure, the number of ALP-positive osteoblast nodules (ratio to control) is shown in mean±standard deviation (n=3). In the Figure, "*" means significant than control at $p<0.05$, and "**" means significant than control at $p<0.01$.

As the observation results with a microscope, the number of osteoblast nodule (ALP-positive osteoblast nodule) stained with ALP when cultured with addition of each of F2 and F2a is shown in FIG. 1 as the ratio to the number of the cell nodule of the control. As regards the aforementioned ratio, an unpaired t-test was performed between the group added with each of F2 and F2a and the control.

As shown in FIG. 1, when cultured by adding each of F2 and F2a, a concentration-dependent differentiation accelerating action on osteoblast was found at a final concentration of not less than 2.5 µM, and a significant difference from the control ($p<0.05$ or $p<0.01$) was found at a final concentration of 5 µM and 10 µM.

Also, when cultured by adding F2a at a final concentration of 5 µM, the expression levels of each gene of transcription factors (Runx2 and Osterix (Osx)) to be the differentiation markers of the osteoblasts and of proteins (Type I collagen, alkaline phosphatase, osteocalcin) were respectively quantified by the RT-PCR method on day 4 of culture, and the ratios to β-actin are shown in Table 1. As regards the expression level of each gene, an unpaired t-test was performed with the control.

TABLE 1

| Osx (to β-actin) | | Runx2 (to β-actin) | | type I collagen (to β-actin) | | alkaline phosphatase (to β-actin) | | osteocalcin (to β-actin) | |
|---|---|---|---|---|---|---|---|---|---|
| control | F2a | control | F2a | control | F2a | control | F2a | control | F2a |
| 0.000503 ± 0.000080 | 0.000685 ± 0.000050* | 0.001931 ± 0.00032 | 0.00182 ± 0.00021 | 0.185 ± 0.044 | 0.154 ± 0.016 | 0.003061 ± 0.00030 | 0.00572 ± 0.00131* | 0.00002021 ± 0.0000106 | 0.0000530 ± 0.0000151* |

*1; The expression level of each gene is shown in mean ± standard deviation (n = 3).
*2; In the Table, "*" means a significant difference than control at $p < 0.05$.

In Table 1, it is found that the gene expression of Osx, alkaline phosphatase and osteocalcin significantly increased in a group added with F2a as compared to the control.

That is, when cultured for 4 days with addition of F2a at a final concentration of 5 µM, it was shown that the gene expression of a transcription factor and protein to be a differentiation marker of osteoblast was accelerated as compared to the control, and it was confirmed that the differentiation of osteoblast is accelerated by 3',4',7-trihydroxyflavanone which is an aglycon of flavanone glycoside derived from *Chamaecrista nomame*.

Experimental Example 2

Study of Influence of Flavanones Derived from *Chamaecrista nomame* on Differentiation of Osteoclast Influence of the flavanone glycoside (F2) derived from *Chamaecrista nomame* obtained in the above-mentioned Production Example and aglycon thereof (F2a) on the differentiation of osteoclast was studied.

Mouse bone marrow cells were seeded in each well of a microplate containing 0.5 mL α-MEM (manufactured by MP Biomedicals INC.) at 3.5×10$^6$ cells/well, and cultured at 37° C., carbon dioxide concentration=5(v/v)%. On day 1 of culture, each of F2 and F2a was added to a concentration of 1 µM, 2.5 µM, 5 µM or 10 µM, and culture was continued. On days 1 and 4 of culture, a differentiation induction reagent (calcitriol) was added to a final concentration of 10 nM. At 6 days from the culture, the cells were stained with tartaric acid resistance acidic phosphatase (TRAP), observed with a microscope (inverted culture microscope "CK40", manufactured by Olympus Corporation, magnification=40×), and the cells stained with TRAP, i.e., differentiated osteoclasts, were detected. The case where neither F2 nor F2a was added was taken as a control.

Figure 2:
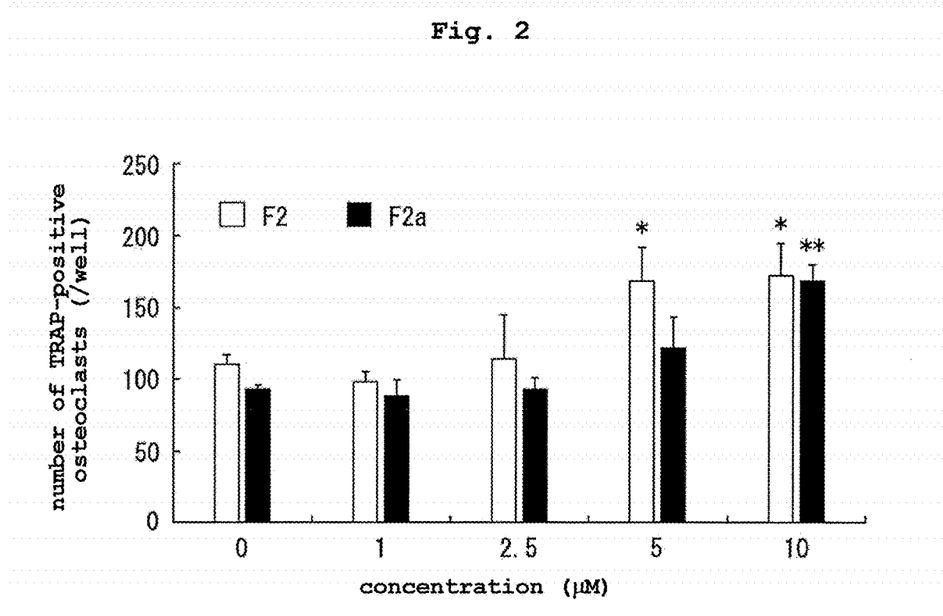
FIG. 2 shows the study results of Experimental Example 2. In the Figure, the number of TRAP-positive osteoclasts (/well) is shown in mean±standard deviation (n=3). In the Figure, "*" means significant than control at $p<0.05$, and "**" means significant than control at $p<0.01$.

As the observation results, the number of osteoclasts stained with TRAP per well (TRAP-positive osteoclast number) is shown in FIG. 2. As regards the aforementioned cell number, an unpaired t-test was performed between the group added with each of F2 and F2a and the control.

As shown in FIG. 2, F2 added at a final concentration of 2.5 µM or more, and F2a added at a final concentration of 5 µM or more exhibited a concentration-dependent differentiation accelerating action on osteoclast, and a significant difference of p<0.05 was found between a group added with F2 at a final concentration of 5 µM and 10 µM and the control, and a significant difference of p<0.01 was found between a group added with F2a at a final concentration of 10 µM and the control.

Experimental Example 3

Study of Influence of Flavanone Derived from *Chamaecrista nomame* on Bone Mass of Vertebral Body of Ovary Excised Mouse Using ovary excised mouse as an animal model of postmenopausal osteoporosis, influence of 3',4',7-trihydroxyflavanone (F2a) obtained in the above-mentioned Production Example which is an aglycon of flavanone glycoside derived from *Chamaecrista nomame* on the bone mass of the vertebral body was studied.

The ovary of ddY mice (female, 7-week-old) was excised, and the mice (OVX mouse) were divided into 4 groups (n=6/group) and bred for 4 weeks. To the control group was orally administered purified water (0.1 mL) once per day for 4 weeks. In the 3 groups to be administered with F2a, F2a was orally administered at 3 mg/kg body weight, 10 mg/kg body weight or 30 mg/kg body weight once per day for 4 weeks. On the other hand, in a sham operation group (n=6), a sham operation was performed, the mice were bred for 4 weeks, and purified water (0.1 mL) was orally administered once per day for 4 weeks.

Figure 3:
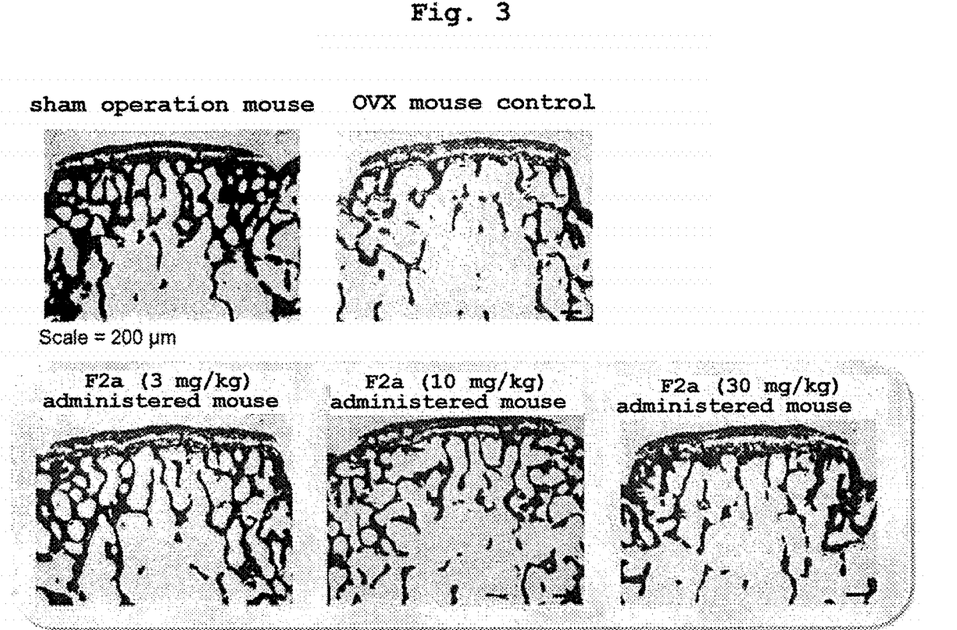
FIG. 3 shows Von Kossa staining image of non-decalcified thin section of the spine of the mice of each group in Experimental Example 3. In the Figure, the bar indicates the scale (200 μm).

Then, the spine was isolated from each group of the mouse, and frozen specimens were prepared. Non-decalcified sliced specimen were obtained, the calcified part was stained by Von Kossa staining, and the morphology of the cancellous bone was observed with a microscope (inverted culture microscope "CK40", manufactured by Olympus Corporation, magnification=40×). The stained images of cancellous bone in the specimens of each group are shown in FIG. 3.

Figure 4:
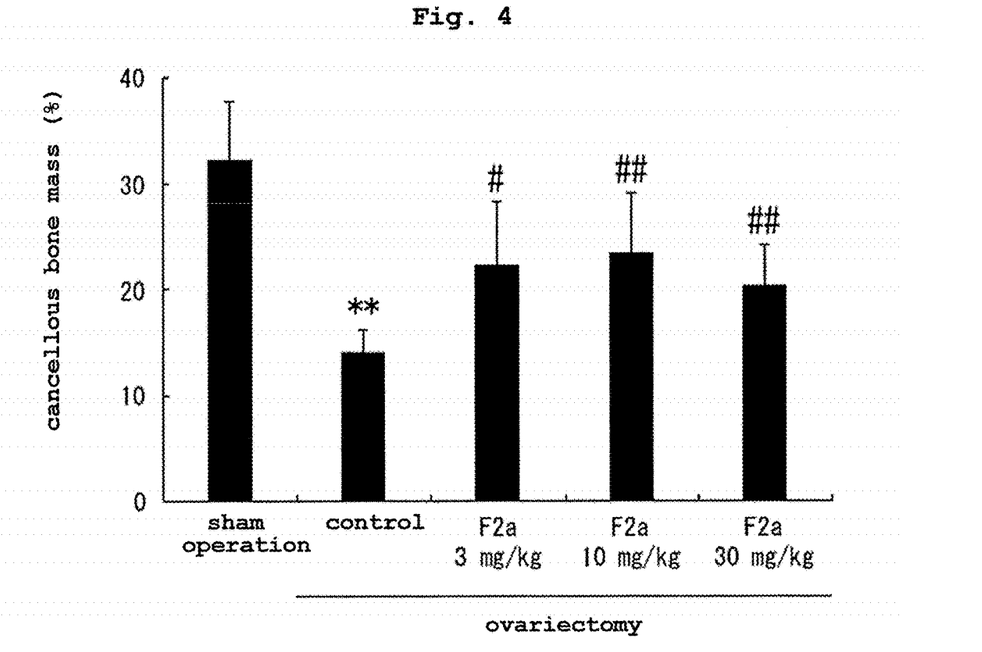
FIG. 4 shows the measurement results of cancellous bone mass of the vertebral body of the mice of each group in Experimental Example 3. The measurement results of the cancellous bone mass are shown in mean±standard deviation (n=6). In the Figure, "**" means significant than sham operation group at $p<0.01$, "#" means significant than control group at $p<0.05$, and "##" means significant than control at $p<0.01$.
Figure 5:
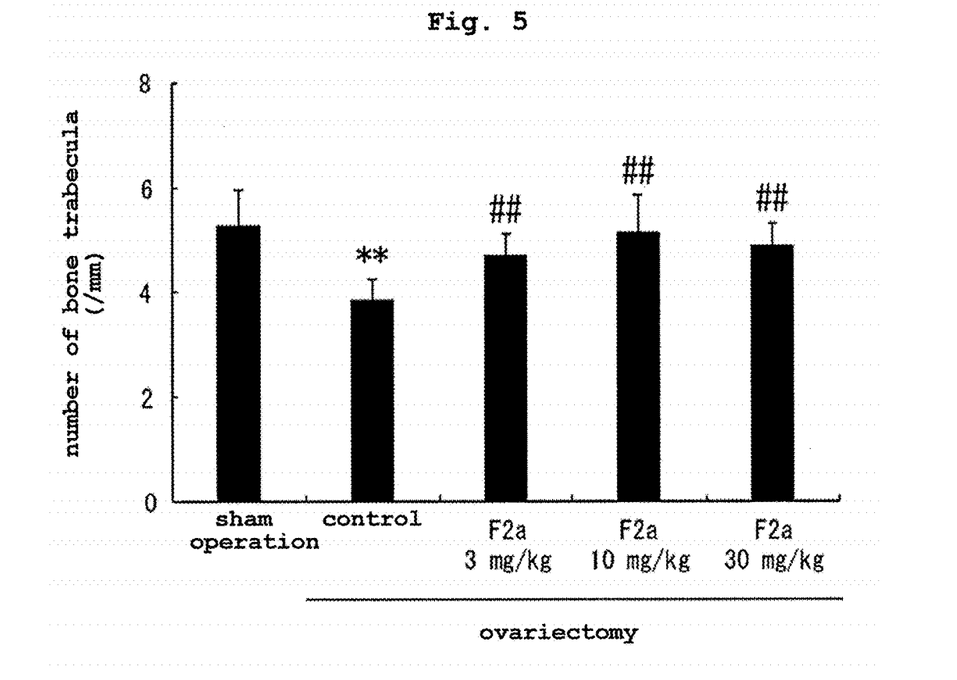
FIG. 5 shows the measurement results of the number of bone trabecula of the vertebral body of the mice of each group in Experimental Example 3. The measurement results of the number of bone trabecula are shown in mean±standard deviation (n=6). In the Figure, "**" means significant than sham operation group at $p<0.01$, and "##" means significant than control group at $p<0.01$.
Figure 6:
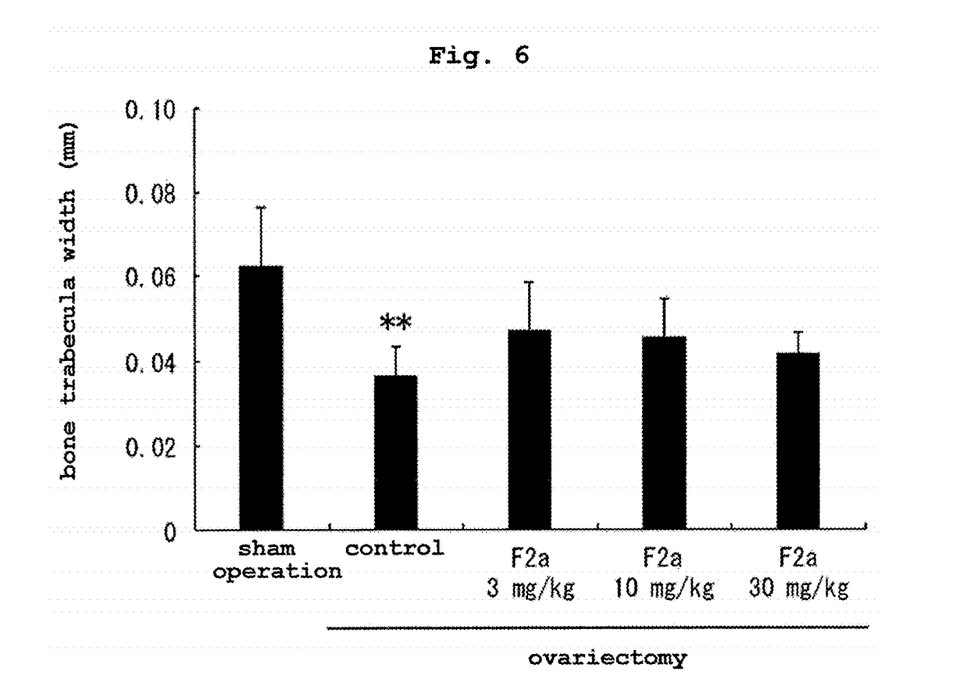
FIG. 6 shows the measurement results of the width of bone trabecula of the vertebral body of the mice of each group in Experimental Example 3. The measurement results of the width of bone trabecula are shown in mean±standard deviation (n=6). In the Figure, "**" means significant than sham operation group at $p<0.01$.

From the above-mentioned observation images under the microscope, the cancellous bone mass, bone trabecula number and bone trabecula width of each group were determined and shown in FIGS. 4-6. As for the cancellous bone mass, bone trabecula number and bone trabecula width, an unpaired t-test was performed between the control group and sham operation group, and each amount of F2a administration group and the control group.

Figure 7:
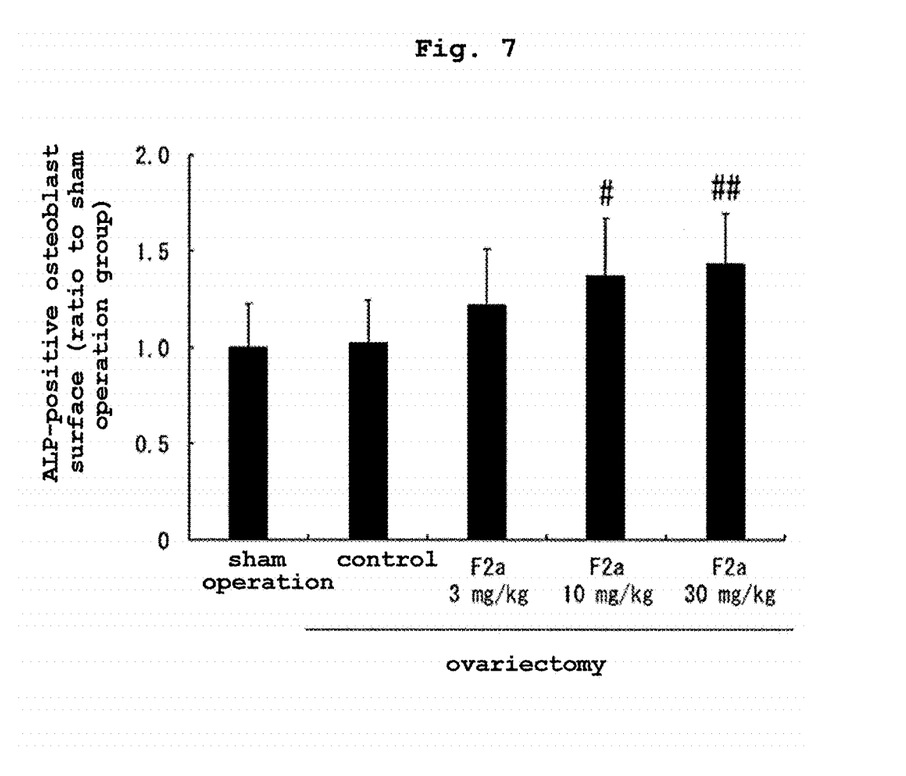
FIG. 7 shows the measurement results of ALP-positive osteoblast surface on cancellous bone surface of the vertebral body of the mice of each group (ratio to sham operation group) in Experimental Example 3. The measurement results of the ALP-positive osteoblast surface are shown in mean±standard deviation (n=6). In the Figure, "#" means significant than control group at $p<0.05$, and "##" means significant than control at $p<0.01$.
Figure 8:
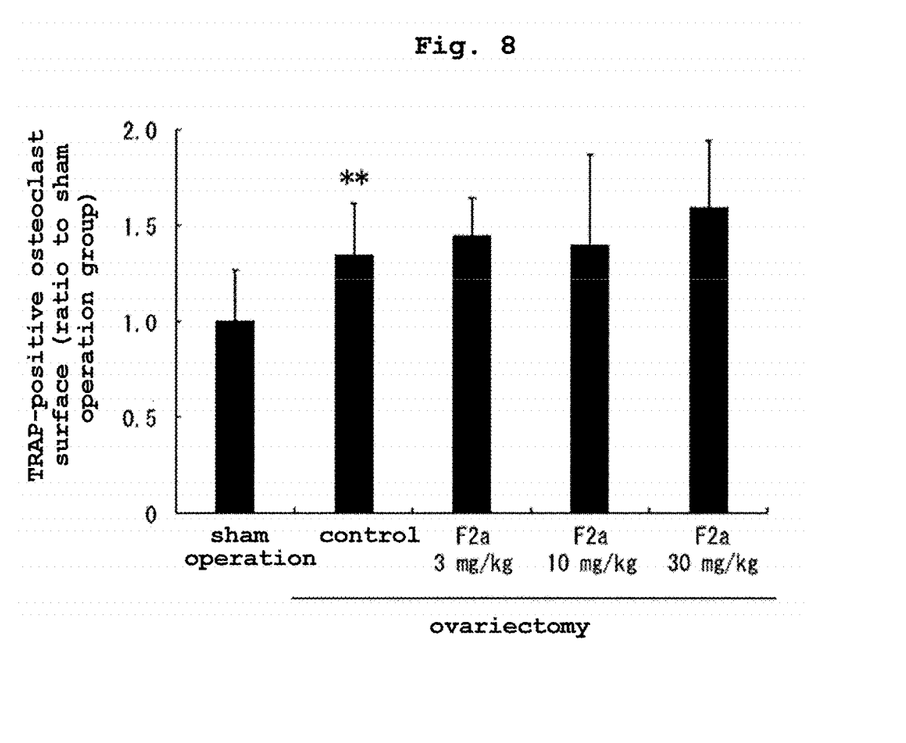
FIG. 8 shows the measurement results of TRAP-positive osteoclast surface on cancellous bone surface of the vertebral body of the mice of each group (ratio to sham operation group) in Experimental Example 3. The measurement results of the TRAP-positive osteoclast surface are shown in mean±standard deviation (n=6). In the Figure, "**" means significant than sham operation group at $p<0.01$.

Furthermore, non-decalcified slice specimen was stained with ALP and the osteoblast stained with ALP was observed with a microscope (inverted culture microscope "CK40", manufactured by Olympus Corporation, magnification=200×). The non-decalcified slice specimen was stained with TRAP and the osteoblast stained with TRAP was observed with a microscope (inverted culture microscope "CK40", manufactured by Olympus Corporation, magnification=200×). From these observation images under the microscopes, the ratio of area of ALP-positive osteoblasts on the bone surface (ALP-positive osteoblast surface) (%) and the ratio of area of TRAP-positive osteoblasts on the bone surface (TRAP-positive osteoclast surface) (%) were determined for each group, and the ratios to those of the sham operation group are shown in FIG. 7 and FIG. 8.

As for the measurement results of the ALP-positive osteoblast surface and the TRAP-positive osteoclast surface, an unpaired t-test was performed between the control group and the sham operation group, and respective amounts of the F2a administration group and the control group.

In FIG. 3, OVX mouse showed a clear decrease in the cancellous bone mass of the vertebral body as compared to the sham operated mouse.

In contrast, it was found that oral administration of each amount of F2a increased the cancellous bone mass of the vertebral body.

As shown in FIGS. 4-6, it was found that excision of the ovary significantly decreased all of cancellous bone mass, bone trabecula number and bone trabecula width as compared to the sham operation group ($p<0.01$).

Oral administration of F2a to OVX mouse showed a significant increase in the cancellous bone mass and bone trabecula number ($p<0.05$ or $p<0.01$), and oral administration of 10 mg/kg body weight showed the highest increase. While the bone trabecula width did not show a significant difference, it showed a tendency toward increase by the oral administration of F2a.

As shown in FIG. 7 and FIG. 8, excision of the ovary did not show a change on the ALP-positive osteoblast surface; however, the TRAP-positive osteoclast surface significantly decreased as compared to the sham operation group ($p<0.01$).

Among the groups with oral administration of F2a to OVX mouse, a group with oral administration of F2a at not less than 10 mg/kg body weight showed a significant increase in the ALP-positive osteoblast surface ($p<0.05$ or $p<0.01$). A significant difference as compared to the control group was not found in the TRAP-positive osteoclast surface; however, a tendency toward increase was found in the F2a oral administration group.

From the results shown in FIGS. 3-8, a possibility that osteoporosis may be improved by oral administration of 3',4',7-trihydorxyflavanone which is an aglycon of flavanone glycoside derived from *Chamaecrista nomame* was suggested.

From the results of the above-mentioned Experimental Examples 1-3, it is suggested that flavanone glycoside derived from *Chamaecrista nomame*, or aglycon thereof may be able to accelerate bone remodeling and improve osteoporosis by promoting differentiation of both osteoblast and osteoclast.

INDUSTRIAL APPLICABILITY

As described above, according to the present invention, a bone remodeling accelerator that can favorably accelerate differentiation of both osteoblast and osteoclast, and can accelerate bone remodeling by promoting bone resorption and bone formation in good balance can be provided.

The bone remodeling accelerator of the present invention accelerates bone metabolism and is useful for preventing or improving osteoporosis or a decrease in bone strength.

This application is based on a patent application No. 2017-181670 filed in Japan, the contents of which are incorporated in full herein.

The invention claimed is:

1. A method for accelerating bone remodeling without inhibiting bone resorption, comprising administering an effective amount of 3',4',7-trihydroxyflavanone, a glycoside thereof, or a combination thereof to a subject in need thereof, wherein the effective amount is 3 mg-150 mg per day as the amount of 3',4',7-trihydroxyflavanone for a human adult.

2. The method according to claim 1, wherein the 3',4',7-trihydroxyflavanone and the glycoside thereof are flavanone of a plant belonging to the genus Chamaecrista and a glycoside thereof.

3. The method according to claim 1, wherein the 3',4',7-trihydroxyflavanone and the glycoside thereof are contained as an extract of a plant belonging to the genus Chamaecrista in methanol and ethyl acetate.

4. A method for preventing or improving osteoporosis or a decrease in bone strength without inhibiting bone resorption, administering an effective amount of 3',4',7-trihydroxyflavanone, a glycoside thereof, or a combination thereof to a subject in need thereof, wherein the effective amount is 3 mg-150 mg per day as the amount of 3',4',7-trihydroxyflavanone for a human adult.

5. The method according to claim 4, wherein the 3',4',7-trihydroxyflavanone and the glycoside thereof are flavanone of a plant belonging to the genus Chamaecrista and a glycoside thereof.

6. The method according to claim 4, wherein the 3',4',7-trihydroxyflavanone and the glycoside thereof are contained as an extract of a plant belonging to the genus Chamaecrista in methanol and ethyl acetate.

* * * * *